(12) United States Patent
Cho

(10) Patent No.: US 12,370,384 B2
(45) Date of Patent: Jul. 29, 2025

(54) MULTI-FOCUSING DEVICE FOR EACH ULTRASONIC DEPTH INCLUDING MICRO-MACHINED ULTRASONIC TRANSDUCER ARRAY AND METHOD OF OPERATING SAME

(71) Applicant: MUTI Inc., Daejeon (KR)

(72) Inventor: Kyung Il Cho, Daejeon (KR)

(73) Assignee: MUTI Inc., Daejeon (KR)

( * ) Notice: Subject to any disclaimer, the term of this patent is extended or adjusted under 35 U.S.C. 154(b) by 0 days.

(21) Appl. No.: 18/001,489

(22) PCT Filed: Feb. 10, 2022

(86) PCT No.: PCT/KR2022/002026
§ 371 (c)(1),
(2) Date: Dec. 12, 2022

(87) PCT Pub. No.: WO2022/211264
PCT Pub. Date: Oct. 6, 2022

(65) Prior Publication Data
US 2024/0009489 A1 Jan. 11, 2024

(30) Foreign Application Priority Data
Mar. 30, 2021 (KR) .................. 10-2021-0040793

(51) Int. Cl.
*A61N 7/02* (2006.01)
*A61N 7/00* (2006.01)
(52) U.S. Cl.
CPC ........ *A61N 7/02* (2013.01); *A61N 2007/0034* (2013.01); *A61N 2007/0078* (2013.01); *A61N 2007/0095* (2013.01); *A61N 2007/027* (2013.01)

(58) Field of Classification Search
CPC .............. A61N 7/02; A61N 2007/0034; A61N 2007/0078; A61N 2007/0095; A61N 2007/027
See application file for complete search history.

(56) References Cited

U.S. PATENT DOCUMENTS

2009/0182237 A1* 7/2009 Angelsen ............ B06B 1/064
600/459
2018/0345045 A1* 12/2018 Barthe .................. A61N 7/00

FOREIGN PATENT DOCUMENTS

JP 2020-189082 A 11/2020
KR 10-2016-0069293 A 6/2016
(Continued)

OTHER PUBLICATIONS

May 20, 2022 (WO) English Translation of International Search Report PCT/KR2022/002026.

*Primary Examiner* — Chao Sheng
(74) *Attorney, Agent, or Firm* — CHRISTENSEN O'CONNOR JOHNSON KINDNESS PLLC

(57) ABSTRACT

Disclosed are a multi-focusing device for each ultrasonic depth including a micro-machined ultrasonic transducer array and a method of operating the same. The multi-focusing device includes a micro-machined ultrasonic transducer (MUT) array arranged in an annular form and formed of a plurality of vibration elements that apply a low or high frequency corresponding to an application depth inside the skin, wherein the MUT array includes an upper electrode parallel connection line configured for each channel of the vibration element, and a lower electrode connection line arranged in a longitudinal direction.

15 Claims, 7 Drawing Sheets

(56) References Cited

FOREIGN PATENT DOCUMENTS

| | | |
|---|---|---|
| KR | 10-2017-0063460 A | 6/2017 |
| KR | 10-2020-0109496 A | 9/2020 |
| KR | 10-2020-0116083 A | 10/2020 |
| WO | 2013165706 A2 | 11/2013 |

* cited by examiner

MULTI-FOCUSING DEVICE FOR EACH ULTRASONIC DEPTH INCLUDING MICRO-MACHINED ULTRASONIC TRANSDUCER ARRAY AND METHOD OF OPERATING SAME

RELATED APPLICATIONS

This application is a National Stage Application under 35 U.S.C. 371 of co-pending PCT application PCT/KR2022/002026 designating the United States and filed Feb. 10, 2022; which claims the benefit of KR application number 10-2021-0040793 and filed Mar. 30, 2021, each of which are hereby incorporated by reference in their entireties.

TECHNICAL FIELD

The present disclosure relates to a multi-focusing device for each ultrasonic depth including a micro-machined ultrasonic transducer array and a method of operating the same, and more particularly, to a multi-focusing device for each ultrasonic depth which uses a large-area multi-channel micro-machined ultrasonic transducer array for therapy through stimulation inside skin.

BACKGROUND ART

Recently, many devices that use high frequency or low frequency to be expected to have a skin beauty or massage effect have been proposed and released. As such, as life is improved according to industrial development, interest in skin beauty, health, or body care is increasing, and various therapy devices reflecting these needs have been released.

Existing ultrasound therapy devices may be largely classified into home therapy devices and hospital therapy devices.

The home therapy device mainly uses two types of low-frequency ultrasound, 1 MHz or 3 MHz, and uses a single channel ultrasound beam, so the effect is limited for users at home.

Meanwhile, the hospital therapy device mainly uses low-frequency (1 MHz or 3 MHz) and high-frequency (10 MHz) ultrasound, and because the hospital therapy device uses multiple channels of ultrasound beams, the focus of the beam is customized to the depth of each user's skin. However, a so-called high intensity focused ultrasonic (HIFU), which is mainly used for hospitals, is expensive and has the inconvenience of requiring a user to visit a hospital for treatment.

DETAILED DESCRIPTION OF THE INVENTION

Technical Problem

An object of the present disclosure is to provide a device for focusing a high-frequency or low-frequency ultrasound beam at an application depth inside skin by using a plurality of vibration elements formed in a multi-channel micro-machined ultrasonic transducer array.

In addition, an object of the present disclosure is to minimize the signal voltage drop by disposing connection lines on each of upper and lower electrodes formed of a plurality of vibration elements arranged in an annular shape on a chip, and provide a customized focusing function for a specific location by using a reflected signal reflected from a specific location of the human body of each individual.

Technical Solution

According to one aspect of the present invention, there is provided a multi-focusing device for each depth of large-area multi-channel ultrasound for therapy through stimulation inside skin, which includes a micro-machined ultrasonic transducer (MUT) array arranged in an annular form and formed of a plurality of vibration elements that apply a low or high frequency corresponding to an application depth inside the skin, wherein the MUT array includes an upper electrode parallel connection line configured for each channel of the vibration element, and a lower electrode connection line arranged in a longitudinal direction.

According to another aspect of the present invention, there is provided a method of operating a multi-focusing device for each depth of large-area multi-channel ultrasound for therapy through stimulation inside skin, which includes performing beam focusing transmission into the skin through a micro-machined ultrasonic transducer (MUT) array, wherein the MUT array is arranged in an annular form and formed of a plurality of vibration elements that apply a low or high frequency corresponding to an application depth inside the skin; receiving a pulse echo reflected from a specific location inside the skin through a reception element located in a central portion of the MUT array; calculating a signal value for each transmission focusing depth using a received signal and custom-focusing a transmission signal according to a calculation result; and applying the transmission signal through the MUT array.

Advantageous Effects of the Invention

According to the embodiments of the present disclosure, it is possible to focus a high-frequency or low-frequency ultrasound beam at an application depth inside skin by using a plurality of vibration elements formed in a multi-channel micro-machined ultrasonic transducer array.

In addition, according to the embodiments of the present disclosure, it is possible to minimize the signal voltage drop by disposing connection lines on each of upper and lower electrodes formed of a plurality of vibration elements arranged in an annular shape on a chip, and provide a customized focusing function for a specific location by using a reflected signal reflected from a specific location of the human body of each individual.

In addition, according to the embodiments of the present disclosure, by linking the multi-focusing device for each ultrasonic depth with a mobile device, it is possible to enable personalized treatment according to personal skin information and use the multi-focusing device for each ultrasonic depth for a long time at home without visiting a hospital.

BEST MODE

Figure 1:
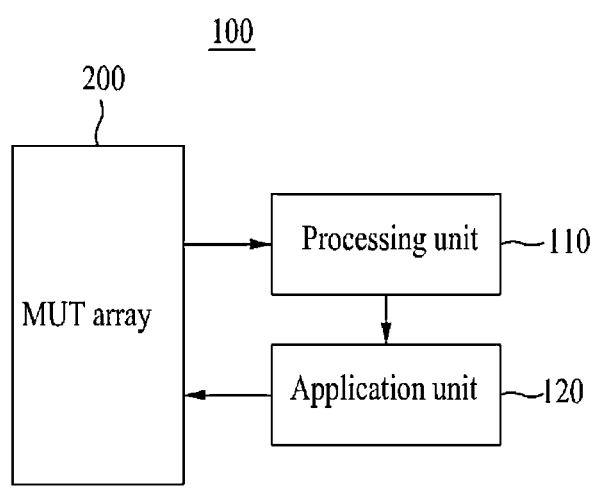
FIG. 1 is a block diagram illustrating a detailed configuration of a multi-focusing device for each ultrasonic depth according to an embodiment of the present disclosure.

Advantages and features of embodiments of the present disclosure, and method for achieving thereof will be apparent with reference to the accompanying drawings and detailed description that follows. But, it should be understood that the present disclosure is not limited to the following embodiments and may be embodied in different ways, and that the embodiments are given to provide complete disclosure of the present disclosure and to provide thorough understanding of the present disclosure to those skilled in the art, and the scope of the present disclosure is limited only by the accompanying claims and equivalents thereof.

The terms used in the present disclosure are provided to describe embodiments, not intended to limit the present disclosure. In the present disclosure, singular forms are intended to include plural forms unless the context clearly indicates otherwise. It will be further understood that the terms "includes," "including," "comprises," and/or "comprising," used herein, specify the presence of stated features, integers, steps, operations, elements, and/or components, but do not preclude the presence or addition of one or more other features, integers, steps, operations, elements, components, and/or groups thereof.

Unless otherwise defined, all terms used herein (including technical or scientific terms) have the same meanings as those generally understood by those skilled in the art to which the present disclosure pertains. Such terms as those defined in a generally used dictionary are not to be interpreted as having ideal or excessively formal meanings unless defined clearly and specifically.

Hereinafter, exemplary embodiments of the present disclosure will be described in detail with reference to the accompanying drawings. The same reference numerals are used for the same components in the drawings, and duplicate descriptions of the same components are omitted.

As the gist of embodiments of the present disclosure, there is provided a multi-focusing device for each ultrasonic depth that focuses on a specific location by using a reflected signal reflected from a specific location of the human body, where vibration elements that focus a high-frequency or low-frequency ultrasound beam are disposed on the chip in an annular shape for therapy through stimulation deep in the skin/muscle/blood flow.

According to an embodiment of the present disclosure, a multi-focusing device for each ultrasonic depth may use a micro-machined ultrasonic transducer (MUT) array including a plurality of channels arranged in an annular shape on a single chip to control focus by depth according to electronic time delay, and may focus a high-frequency or low-frequency ultrasound beam to an application depth inside the skin.

Hereinafter, an embodiment of the present disclosure will be described in detail with reference to FIGS. 1 to 7.

Figure 5:
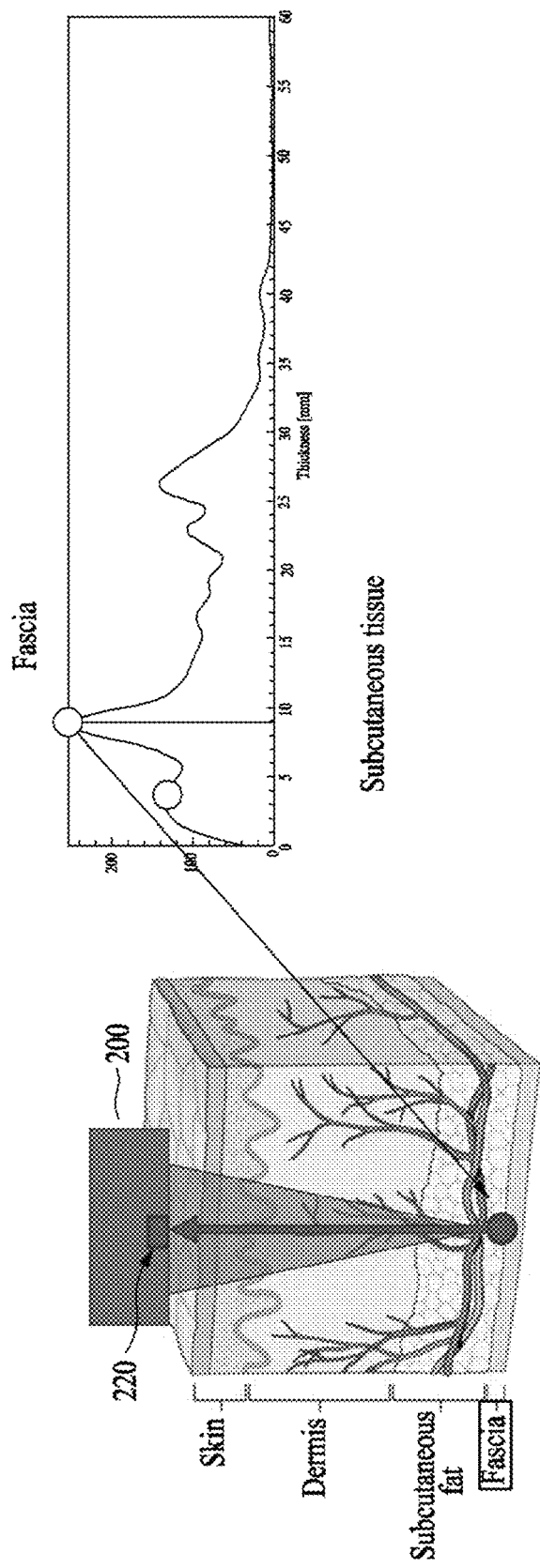
FIG. 5 is a diagram illustrating an example of a customized focus for a specific location according to an embodiment of the present disclosure.
Figure 6:
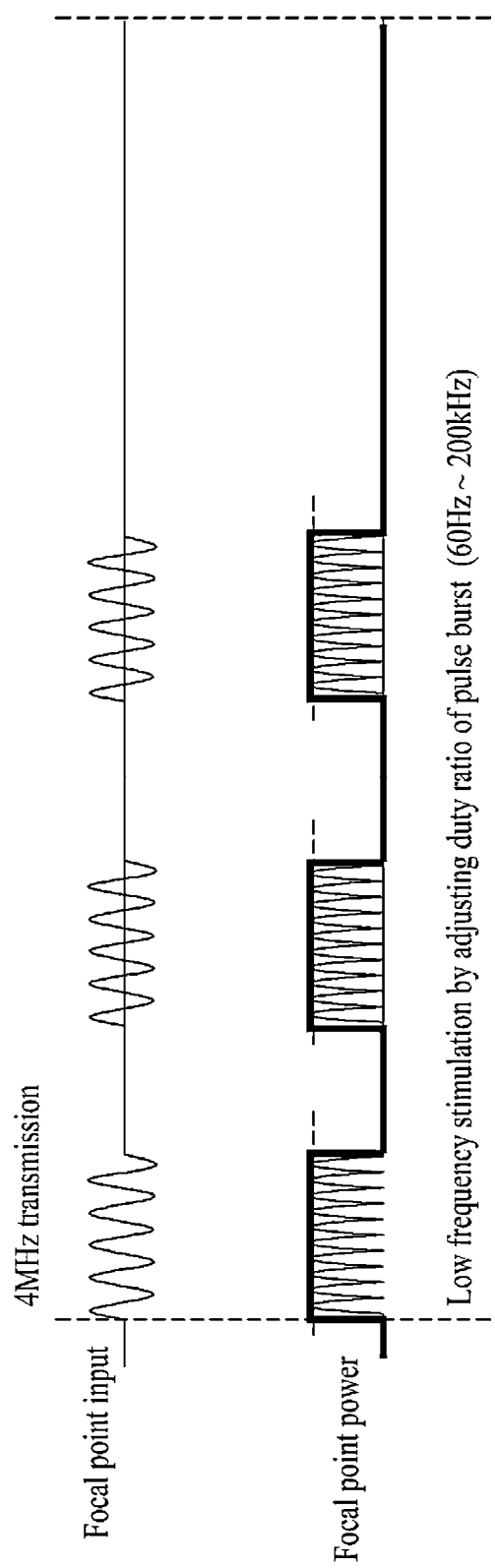
FIG. 6 is a diagram illustrating an adjustment of a duty ratio of an ultrasonic pulse burst according to an embodiment of the present disclosure.

FIG. 1 is a block diagram illustrating a detailed configuration of a multi-focusing device for each ultrasonic depth according to an embodiment of the present disclosure. FIG. 5 is a diagram illustrating an example of a customized focus for a specific location according to an embodiment of the present disclosure. FIG. 6 is a diagram illustrating an adjustment of a duty ratio of an ultrasonic pulse burst according to an embodiment of the present disclosure.

Referring to FIG. 1, a multi-focusing device for each ultrasonic depth according to an embodiment of the present disclosure uses a large-area multi-channel micro-machined ultrasonic transducer array for therapy through stimulation inside the skin and multi-focuses by depth.

To this end, a multi-focusing device 100 for each ultrasonic depth according to an embodiment of the present disclosure includes a MUT array 200, a processing unit 110, and an application unit 120.

The multi-focusing device 100 for each ultrasonic depth according to an embodiment of the present disclosure may include a main body which is assembled in a housing that is easy for a user to carry and attach by hand, and is in contact with the skin, and a micro-machined ultrasonic transducer (MUT) array 200 is formed in the center. According to an embodiment, the main body of the multi-focusing device 100 for each ultrasonic depth may include at least one or more of a power supply unit that turns on/off the operation, an input unit that changes the low or high frequency according to a user's selection input, or adjusts the therapy time, an output unit for outputting an LED color corresponding to the low or high frequency applied to the skin, and a display unit for displaying the remaining time for therapy.

The MUT array 200 according to an embodiment of the present disclosure may be a piezoelectric MUT (pMUT) including a plurality of vibration elements of the array. In this case, the vibration element, which applies a low frequency or a high frequency of different resonant frequencies, may be a low frequency vibration element or a high frequency vibration element. In this case, the vibration element disposed in the first location of the MUT array 200 applies a low frequency of 5 MHz or less, and the vibration element disposed at the second location of the MUT array 200 applies a high frequency of 5 MHz or more to at least one module. According to an embodiment, the vibration element may have a circular, triangular, quadrangular or polygonal shape, and may have different sizes, diameters, and widths of thin films according to the application of a low or high frequency.

The multi-focusing device 100 for each ultrasonic depth according to an embodiment of the present disclosure includes the MUT array 200 arranged in an annular form and formed of a plurality of vibration elements that apply a low or high frequency corresponding to an application depth inside the skin. The MUT array 200 is located at the lower end of a housing which is in contact with the skin, and includes a plurality of vibration elements that are arranged in each channel at regular intervals on the chip and arranged in an annular shape.

The MUT array 200 may include a plurality of channels in which a plurality of vibration elements are arranged in a preset number, and each channel has vibration elements arranged in at least two or more rows. For the upper electrode and the lower electrode connected to the vibration element, the MUT array 200 includes an upper electrode parallel connection line configured for each channel of the vibration element and a lower electrode connection line arranged in the longitudinal direction.

In addition, the MUT array 200 includes the upper electrode formed in an annular shape between the channels in the upper electrode connection line of the vibration elements arranged in an annular shape on the chip, and further includes the upper electrode parallel connection line of the vibration element configured for each channel by adding a separate electrode line, thereby minimizing the signal voltage drop along the longitudinal direction. This will be described in detail with reference to FIG. 4 below.

In addition, the MUT array 200 may include the lower electrode connection line that connects lower electrodes of the vibration element while crossing an upper electrode reference connection line. In addition, the lower electrode connection line may connect the vibration element including a plurality of channels in the longitudinal direction or the radial direction, and minimize the voltage drop between the lower electrodes by adding an annular connection line to the outer/inner periphery of the MUT array 200 and the outer periphery of the central portion. This will be described in detail with reference to FIG. 3 below.

In addition, the MUT array 200 includes a reception element located in the center of a concentric circle as an independent channel, and the reception element receives the pulse echo generated by a multi-channel transmission element disposed at the first and second locations of the MUT array 200 and reflected at a specific location inside the skin. For example, when a signal transmitted through a transmitting element, which refers to vibration elements connected to the upper electrode for transmission, is reflected at a specific location of the subcutaneous or fascia inside the skin, the reception element, which refers to the vibration element connected to the upper electrode for reception, may receive the reception signal of the reflected pulse echo.

In this case, an embodiment of the present disclosure may minimize the high-amplification reception signal disturbance of the transmission ground portion by separating the multi-channel transmission of the transmission element and the ground of the reception of the reception element.

The processing unit 110 custom-focuses the transmission signal according to the signal value for each transmission focusing depth calculated by the reception signal.

Referring to FIG. 5, the fascia layer is located on the inside of the skin more than the subcutaneous layer. In order to stimulate the fascia layer, an ultrasound signal different from that of the subcutaneous tissue is required, which may differ slightly from person to person. Accordingly, according to an embodiment of the present disclosure, the pulse echo reflected from the fascia through the MUT array 200 may be received through a reception element 220. The processing unit 110 may measure a distance by using a received signal reflected from a specific location of the subcutaneous layer and the fascia layer, and may custom-focus the beam on a specific location for beam focusing stimulation at the specific location. After measuring the arrival time by using the reception signal received at a specific location of the human body that is different for each individual, the processing unit 110 may calculate the distance by dividing the speed, and transmits the beam based on the calculated distance value, thereby providing a specific location customized focusing function for the beam focusing stimulation at the specific location.

The processing unit 110 may measure the arrival time and signal magnitude of the reception signal received at a specific location for each individual to control the transmission beamforming, and may apply the transmission focusing auto-calibration function corresponding to the transducer body contact, skin/muscle thickness and temperature change to custom-focus the transmission signal. In this case, the processing unit 110 may determine the maximum fascia signal value among the pulse echo reflection signals based on the transmission focusing auto-calibration function, and adjust the beamforming value according to the depth of a specific location based on the measured depth value to set the transmission signal.

According to the transmission focusing auto-calibration function, in the first step, the beam is focused by depth using the MUT array 200, and the reception signal of the pulse echo is received using the reception element. In the second step, the processing unit 110 calculates the measurement depth of the subcutaneous layer and fascia signal for each transmission focus depth, and measures the signal value. In the third step, the processing unit 110 determines the maximum fascia signal value among the pulse echo received signals for each transmission focus depth. In this case, when the transmission focus is matched to the fascia, the signal is maximized and set to the beamforming time delay control value, and it is possible to map important parts such as the subcutaneous layer of different depths based on the signal measurement depth value. In the fourth step, the processing unit 110 may set the transmission signal by adjusting the beamforming value tuning for each depth of the region of interest (or specific location) based on the setting value.

In addition, as shown in FIG. 6, the processing unit 110 may implement specific bio-frequency stimulation, that is, a low-frequency stimulation of 60 Hz to 200 kHz by adjusting the duty ratio of an ultrasonic pulse burst.

The application unit 120 applies the transmission signal through the MUT array 200. For example, the application unit 120 may apply a low frequency of 5 MHz or less or a high frequency of 5 MHz or more through the vibration elements constituting the MUT array 200 to focus the ultrasound beam to an application depth inside the skin. According to an embodiment, the application unit 120 may apply a micro-current and an LED together with a low frequency or a high frequency through a vibration element according to a preset transmission time of an ultrasound beam based on a control command by the processing unit 110 at the same time, thereby providing efficient therapy performance.

Figure 2:
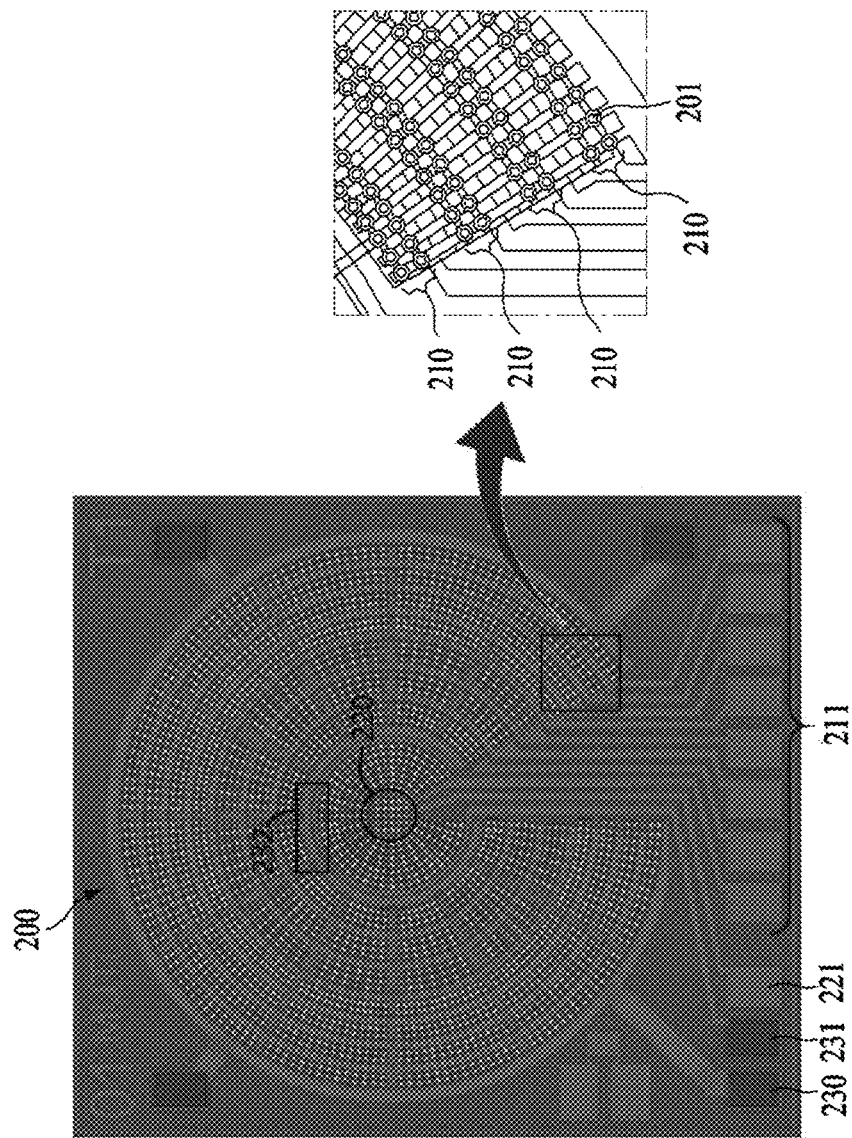
FIGS. 2 to 4 illustrate an example of a micro-machined ultrasonic transducer array according to an embodiment of the present disclosure.
Figure 3:
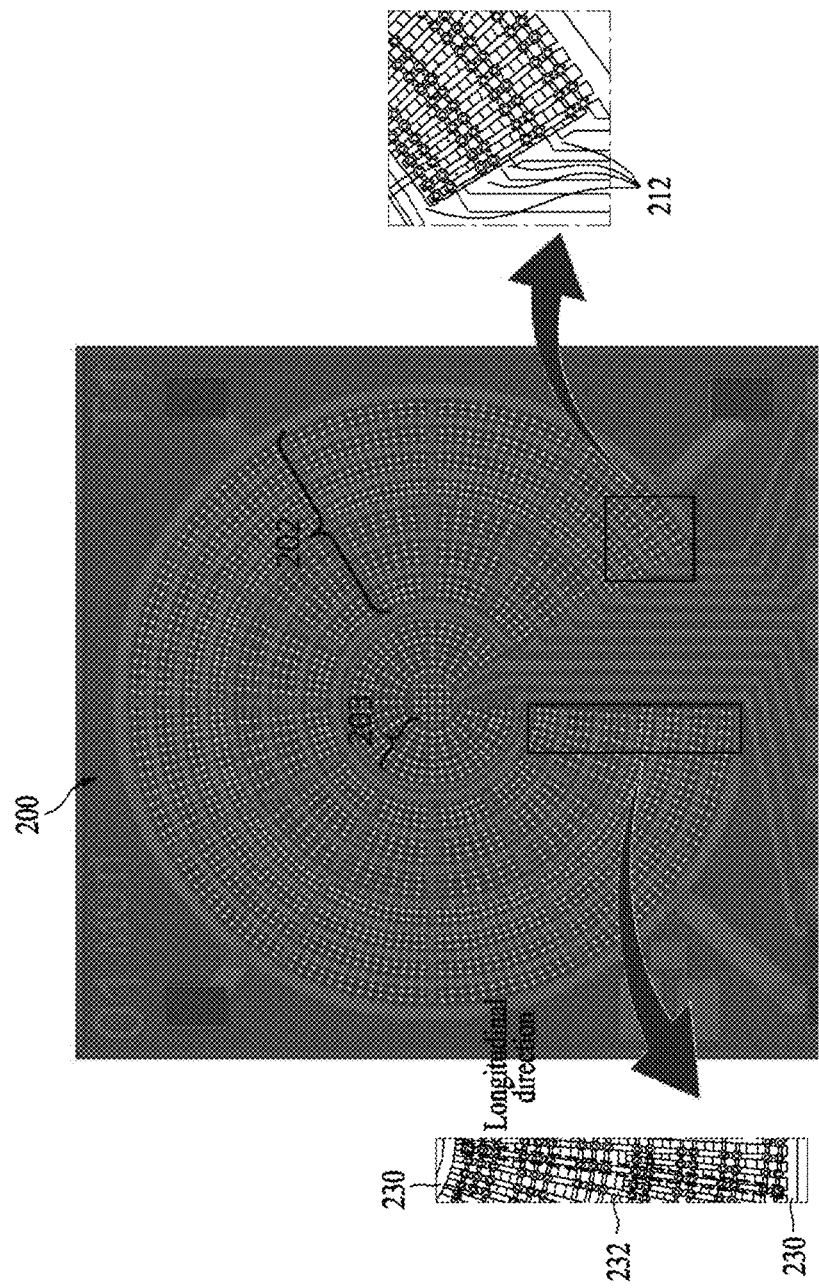
Figure 4:
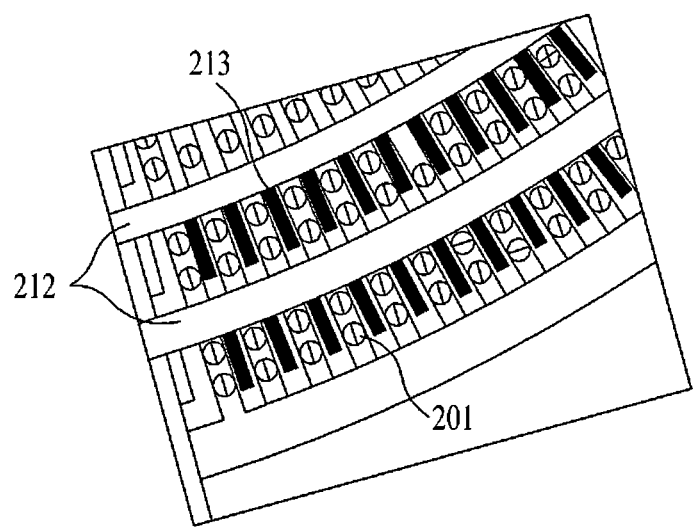

FIGS. 2 to 4 illustrate an example of a micro-machined ultrasonic transducer array according to an embodiment of the present disclosure.

The multi-focusing device 100 for each ultrasonic depth according to an embodiment of the present disclosure includes the MUT array 200 including a plurality of vibration elements on a chip.

Referring to FIGS. 2 and 3, a plurality of vibration elements 201 are arranged at regular intervals to form a channel 210, and the MUT array 200 has a plurality of channels 210 arranged in an annular shape. According to an embodiment, vibration elements may be arranged in at least two or more rows in each channel 210, but the number of vibration elements forming the channel is not limited.

Upper electrodes 211 and 221 and lower electrodes 230 and 231 are connected to each of the plurality of channels 210 formed of the vibration elements 201. In this case, the upper electrode 211 for transmission is connected to the channel 210 disposed in a first location 202 and a second location 203 of the MUT array, and the reception element 220 located as an independent channel in the center of the MUT array is connected to the upper electrode 221 for reception. In this case, the low-frequency vibration element is disposed in the first location 202, and the high-frequency vibration element is disposed in the second location 203.

In addition, the lower electrode includes annular connection lines 230 and 231 at the outer periphery and inner periphery of the MUT array 200 and the outer periphery of the central portion. Accordingly, according to an embodiment of the present disclosure, it is possible to minimize the high-amplification reception signal disturbance of the transmission ground portion by separating 232 the multi-channel transmission of the transmission device which is a low-frequency vibration device formed at the first location 202 and the ground of the reception of the reception element 220.

Referring to FIGS. 3 and 4, in the upper electrode connection line of the vibrating elements 201, a reference connection line 212 is disposed in an annular shape between the channels 210 by the upper electrodes 211 and 221. According to the embodiments of the present disclosure, it is possible to minimize the signal voltage drop in the longitudinal direction by adding an upper electrode parallel connection line 213 which is an electrode line in the form of a horizontal arrangement (or a series arrangement) in a reference connection line 212.

In the lower electrode connection line corresponding to the upper electrode of the vibration elements 201, the lower electrode connection line 232 is disposed in a radial direction (or longitudinal direction) while crossing the upper electrode reference connection line 212 disposed in an annular shape between the channels 210. An embodiment of the present disclosure includes annular connection lines 230 and 231 at the outer and inner periphery of the MUT array 200 and the outer periphery of the central portion. For example, the first annular connection line 230 is disposed in an annular shape on the outer and inner peripheries of the channels 210 disposed at the first location 202, and the second annular connection line 231 is disposed in an annular shape on the outer peripheries of the channels 210 disposed at the second location 203. Accordingly, according to the embodiment of the present disclosure, it is possible to minimize the voltage drop between the lower electrodes.

Figure 7:
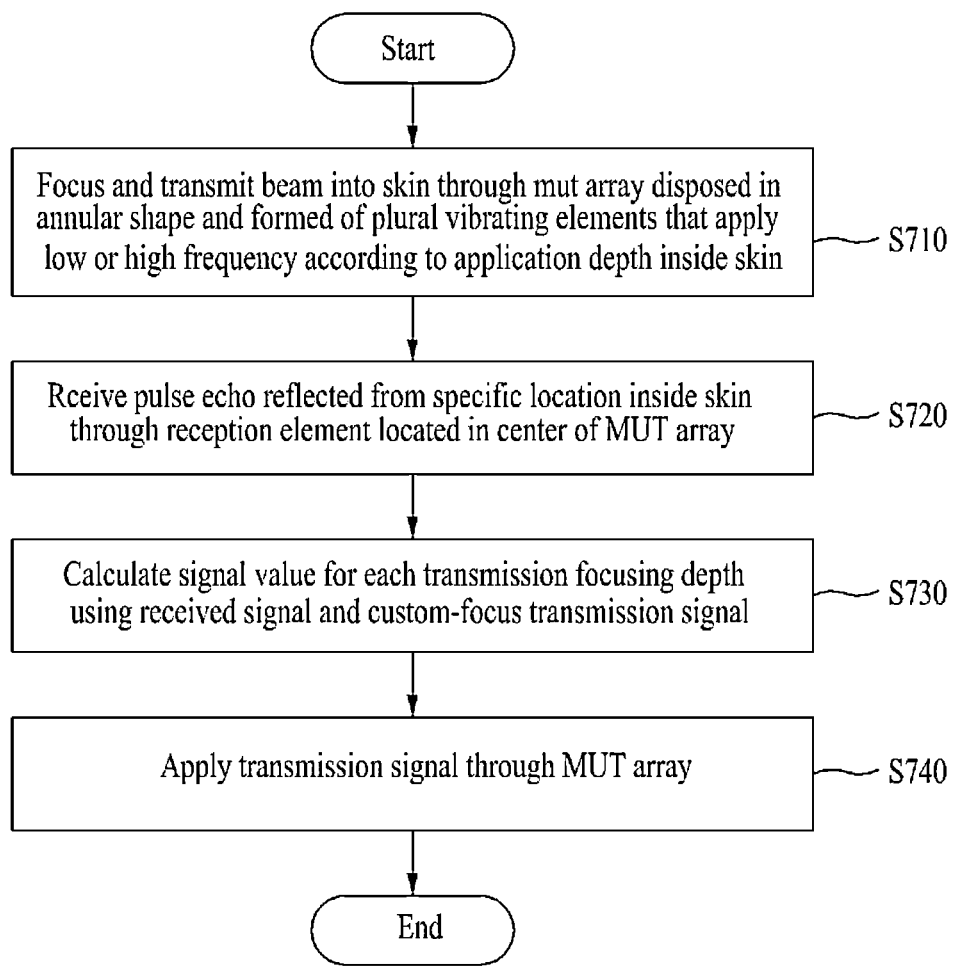
FIG. 7 is a flowchart illustrating a method of operating a multi-focusing device for each ultrasonic depth according to an embodiment of the present disclosure.

FIG. 7 is a flowchart illustrating a method of operating a multi-focusing device for each ultrasonic depth according to an embodiment of the present disclosure.

The method illustrated in FIG. 7 may show a process in which a multi-focusing device for each ultrasonic depth according to an embodiment of the present disclosure operates according to the transmission-focusing auto-calibration function.

Referring to FIG. 7, in operation S710, the beam is focused and transmitted into the skin through the MUT array which is disposed in an annular shape and formed of a plurality of vibrating elements that apply a low frequency or a high frequency according to the application depth inside the skin. In operation S710, the beam may be focused and transmitted to a specific location inside the skin through the transmission elements of the MUT array.

In operation S720, a pulse echo reflected from a specific location inside the skin is received through the reception elements located in the center of the MUT array.

In operation S730, a signal value for each transmission focusing depth is calculated using the received signal, and the transmission signal is custom focused according to the calculation result. In operation S730, the arrival time is measured using the reception signal received at a specific location of the human body, which is different for each individual, and the distance is calculated by dividing the speed. Thus, it is possible to provide a specific location customized focusing function for beam focusing stimulation through transmission to a specific location based on the calculated distance value. In this case, in operation S730, the maximum fascia signal value is determined among the pulse echo reception signals for each transmission focusing depth, and when the transmission focusing is matched to the fascia, it may be set as the beamforming time delay control value of the maximum signal. Then, based on the signal measurement depth value, an important part such as a subcutaneous layer having a different depth may be mapped.

In operation S740, a transmission signal is applied through the MUT array. In operation S840, the transmission signal may be applied by setting a beamforming value for each specific location depth based on the setting value.

The foregoing devices may be realized by hardware elements, software elements and/or combinations thereof. For example, the devices and components illustrated in the exemplary embodiments of the present disclosure may be implemented in one or more general-use computers or special-purpose computers, such as a processor, a controller, an arithmetic logic unit (ALU), a digital signal processor, a microcomputer, a field programmable array (FPA), a programmable logic unit (PLU), a microprocessor or any device which may execute instructions and respond. A processing unit may implement an operating system (OS) or one or software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. Also, the processing unit may have a different processing configuration, such as a parallel processor.

Software may include computer programs, codes, instructions or one or more combinations thereof and may configure a processing unit to operate in a desired manner or may independently or collectively control the processing unit. Software and/or data may be permanently or temporarily embodied in any type of machine, components, physical equipment, virtual equipment, computer storage media or units or transmitted signal waves so as to be interpreted by the processing unit or to provide instructions or data to the processing unit. Software may be dispersed throughout computer systems connected via networks and may be stored or executed in a dispersion manner. Software and data may be recorded in one or more computer-readable storage media.

The methods according to the above-described exemplary embodiments of the present disclosure may be implemented with program instructions which may be executed through various computer means and may be recorded in computer-readable media. The media may also include, alone or in combination with the program instructions, data files, data structures, and the like. The program instructions recorded in the media may be designed and configured specially for the exemplary embodiments of the present disclosure or be known and available to those skilled in computer software. Computer-readable media include magnetic media such as hard disks, floppy disks, and magnetic tape; optical media such as compact disc-read only memory (CD-ROM) disks and digital versatile discs (DVDs); magneto-optical media such as floptical disks; and hardware devices that are specially configured to store and perform program instructions, such as read-only memory (ROM), random access memory (RAM), flash memory, and the like. Program instructions include both machine codes, such as produced by a compiler, and higher level codes that may be executed by the computer using an interpreter. The described hardware devices may be configured to act as one or more software modules to perform the operations of the above-described exemplary embodiments of the present disclosure, or vice versa.

MODE FOR CARRYING OUT THE INVENTION

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Thus, it is intended that the present disclosure covers other realizations and other embodiments of this disclosure provided they come within the scope of the appended claims and their equivalents.

The invention claimed is:

1. A multi-focusing device for each depth of large-area multi-channel ultrasound for therapy through stimulation inside skin, the multi-focusing device comprising:
   a micro-machined ultrasonic transducer (MUT) array arranged in an annular form and formed of a plurality of vibration elements that apply a low or high frequency corresponding to an application depth inside the skin,
   wherein the MUT array includes an upper electrode parallel connection line configured for each channel of the plurality of vibration elements, and a lower electrode connection line.

2. The multi-focusing device of claim 1, wherein the plurality of vibration elements includes a low-frequency vibration element or a high-frequency vibration element.

3. The multi-focusing device of claim 1, wherein the MUT array includes a plurality of channels in which the plurality of vibration elements are arranged in a predetermined number, and wherein each channel includes the vibration elements arranged in at least two or more rows.

4. The multi-focusing device of claim 3, wherein the MUT array includes an upper electrode reference connection line of the plurality of vibration elements formed in an annular shape between the channels, and the upper electrode parallel connection line arranged horizontally based on the upper electrode reference connection line.

5. The multi-focusing device of claim 4, wherein the MUT array includes the lower electrode connection line that connects lower electrodes of the plurality of vibration elements while crossing the upper electrode reference connection line.

6. The multi-focusing device of claim 5, wherein the lower electrode is configured to connect the plurality of vibration elements including a plurality of channels in the longitudinal direction, and constitutes an annular connection line at an outer periphery of the MUT array and an outer periphery of a central portion.

7. The multi-focusing device of claim 1, wherein the MUT array includes a reception element at a central portion as an independent channel.

8. The multi-focusing device of claim 7, wherein the reception element is configured to receive a pulse echo generated by a multi-channel transmitting element disposed at an edge of the MUT array.

9. The multi-focusing device of claim 8, wherein a multi-channel transmission ground of the transmitting element is separated from a ground of receiving of the reception element.

10. The multi-focusing device of claim 7, further comprising:
    a processing unit configured to calculate a signal value for each transmission focusing depth using a received signal received by the reception element, and custom-focus a transmission signal according to calculated results; and
    an application unit configured to apply the transmission signal through the MUT array.

11. The multi-focusing device of claim 10, wherein the processing unit is configured to implement a specific bio-frequency stimulation by adjusting a duty ratio of an ultrasound pulse burst.

12. The multi-focusing device of claim 10, wherein the processing unit is configured to measure a distance using the received signal reflected from a specific location including a subcutaneous layer and a fascia layer inside the skin, and perform the specific location custom focusing for beam focusing stimulation at a specific location.

13. The multi-focusing device of claim 12, wherein the processing unit is configured to control transmission beamforming by measuring an arrival time and a signal magnitude of the received signal received at the specific location for each individual, custom-focus the transmission signal by applying a transmission focusing auto-calibration function corresponding to a transducer body contact, a skin/muscle thickness and a temperature change.

14. The multi-focusing device of claim 13, wherein the processing unit is configured to determine a maximum fascia signal value among pulse echo reflection signals based on the transmission focusing auto-calibration function, and set the transmission signal by adjusting a beamforming value according to a depth of the specific location based on a measured depth value.

15. A method of operating a multi-focusing device for each depth of large-area multi-channel ultrasound for therapy through stimulation inside skin, the method comprising:
    performing beam focusing transmission into the skin through a micro-machined ultrasonic transducer (MUT) array, wherein the MUT array is arranged in an annular form and formed of a plurality of vibration elements that apply a low or high frequency corresponding to an application depth inside the skin;
    receiving a pulse echo reflected from a specific location inside the skin through a reception element located in a central portion of the MUT array;
    calculating a signal value for each transmission focusing depth using a received signal and custom-focusing a transmission signal according to calculated results; and
    applying the transmission signal through the MUT array.

* * * * *